(12) United States Patent
Burov et al.

(10) Patent No.: US 8,350,077 B2
(45) Date of Patent: Jan. 8, 2013

(54) AMIDES OF CREATINE, METHOD OF THEIR PREPARATION, AND REMEDY POSSESSING A NEUROPROTECTIVE ACTIVITY

(75) Inventors: Sergej Vladimirovich Burov, Saint-Petersburg (RU); Natalia Vasilyevna Khromova, Saint-Petersburg (RU); Anna Alexandrovna Khromova, Saint-Petersburg (RU); Petr Alekseevich Khromov, Saint-Petersburg (RU)

(73) Assignee: VERTEX Closed Joint Stock Company, St. Petersburg (RU)

( * ) Notice: Subject to any disclaimer, the term of this patent is extended or adjusted under 35 U.S.C. 154(b) by 0 days.

(21) Appl. No.: 12/734,183

(22) PCT Filed: Dec. 24, 2008

(86) PCT No.: PCT/RU2008/000793
§ 371 (c)(1),
(2), (4) Date: Apr. 15, 2010

(87) PCT Pub. No.: WO2010/074591
PCT Pub. Date: Jul. 1, 2010

(65) Prior Publication Data
US 2011/0269986 A1 Nov. 3, 2011

(51) Int. Cl.
*C07C 229/26* (2006.01)
*C07C 231/00* (2006.01)
*C07C 237/20* (2006.01)

(52) U.S. Cl. ........................................ 560/169; 564/159

(58) Field of Classification Search .................. 564/193, 564/194, 196, 159; 514/626; 560/169
See application file for complete search history.

(56) References Cited

U.S. PATENT DOCUMENTS 6,518,458 B1 * 2/2003 Moinet et al. .................. 564/194
7,816,116 B2 * 10/2010 Nagai et al. .................... 435/227

OTHER PUBLICATIONS

Sherwood et al, JBC., 283(4), 1818-30, 2008.*

* cited by examiner

*Primary Examiner* — Shailendra Kumar
(74) *Attorney, Agent, or Firm* — Aleksandr Smushkovich

(57) ABSTRACT

The invention relates to pharmaceutical chemistry notably to new biologically active substances (BAS) and their properties. In particular, the invention relates to Creatine derivatives having a general formula: $NH=C(NH_2)-N(CH_3)-CH_2-CO-NH-R*X$, wherein R—amino acid residue of aliphatic, aromatic or heteroaromatic L-amino acid or its derivative representing a salts of amino acid, amino acid esters, amino acid amides or peptides; X—lower organic or mineral acid or water. New substances are prepared by interaction of aforesaid amides of sarcosine having a general formula of $HN(CH_3)-CH_2-CO-NH-R*X$, wherein: R is amino acid residue or substituted amino acid residue; X is low-molecular-weight organic acid or mineral acid or water, with a guanidinylating agents with the in organic solvents at temperature not exceeding 50° C. New chemical compounds can be used as a remedy possessing a neuroprotective activity.

3 Claims, No Drawings

AMIDES OF CREATINE, METHOD OF THEIR PREPARATION, AND REMEDY POSSESSING A NEUROPROTECTIVE ACTIVITY

CROSS-REFERENCE TO RELATED APPLICATIONS

This application is a U.S. national stage application of a PCT application PCT/RU2008/000793 filed on 24 Dec. 2008, whose disclosure is incorporated herein in its entirety by reference, which PCT application claims priority of a Russian Federation application RU2007142673/04 filed on 21 Nov. 2008.

FIELD OF THE INVENTION

The invention relates to pharmaceutical chemistry, especially to new biologically active substances (BAS) and their properties. In particular, the invention relates to Creatine derivatives.

BACKGROUND OF THE INVENTION

Creatine (Cr) is an endogenous nutrient that occurs in various tissues of mammalians, for example, in liver, kidneys, muscular tissue, brain tissue, blood, etc.; it appears in a free state, and in the form of Creatine phosphate as well. Creatine is considered a remedy enhancing the energy tissue metabolism that is increasing the energy reserve of ATP, first of all, in the muscular and nerve cells.

In a cell's mitochondria, Creatine interacts reversibly with adenosine triphosphate (ATP), which is caused by the action of the Creatine kinase enzyme with a formation of Creatine phosphate and adenosine diphosphate (ADP). This interaction maintains of the ATP concentration at a constant level at the moments of its intense consumption. There exist other ways for replenishing ATF, such as glycolysis or oxidative phosphorylation, but they refill ATP noticeably slower. Upon consumption of ATP in a cell, a great amount of ADP is released that leads to a transfer of ortho-phosphate from Creatine phosphate to ADP, and the initial ratio between ATP and ADP remains. Due to the high affinity of Creatine kinase to ADP, this process proceeds until a Creatine phosphate concentration falls below several tens μM.

Creatine phosphate (CrP) represents a reserve of macroergic phosphate in maintaining the membrane potential, activation of metabolites or contractive activity of a cell. It maintains the ATP level along with an increasing of energy consumption in a cell, i.e. restores an ortho-phosphate residue on ADP. Like glycogen, CrP is one of the basic sources of the high-energy phosphates transformation cycle, and thereby participates in oxidative phosphorylation of glucose that provides liberation of energy necessary for the functionality of muscular tissue cells, including skeletal muscles and the cardiac muscle. Since Creatine phosphate provides for regenerating ATP with a significant speed, which is achieved by glycogen, an increase of Creatine amount in the muscles raises the muscles capacity of CrP, enhances the muscles workability and increases the muscle bulk.

Creatine phosphate and Creatine are also allosteric regulators of cell processes. It was shown that per os administration of Creatine increases the total Creatine content in an organism. So, administration of Creatine monohydrate at dosages up to 30 g for a few days causes an increase of the total Creatine content in a human's skeleton muscles by more than 20%. These properties attract a special attention due to the possibility of usage of Creatine monohydrate as a food additive for organism enforcement and increase of workability especially in its usage as an addition to the sportsman diet. So, administering Creatine monohydrate in a daily dose 15 g for at least 2 days is used for increasing the muscle force (WO 94/02127, 1994). Nowadays Creatine is recommended as a food additive that is especially important for aged people and vegetarians as there is an expressed tendency to decreasing the Creatine level in the muscles at these groups. The additives are used as a dry powder, liquid or in a semi-liquid form (WO 97/45026, 1997). The composition prepared on their basis are stable in the refrigerator at a temperature of (+)4° C. for a long time, but it degrades at the room temperature during one week.

Besides the use in the food industry, Creatine and Creatine phosphate have wide applications in medicine. For example, Creatine, Creatine phosphate, and cyclo-Creatine (U.S. Pat. No. 6,706,764, 2004) are recommended for the treatment of nervous system diseases such as diabetic and toxic neuropathies, Alzheimer's disease, Parkinson's disease, stroke etc., and also disturbances of metabolism as hyperglycemia and diabetes mellitus (U.S. Pat. No. 6,193,973, 2001). Per os administration of Creatine is described to be used for the treatment of cardiac insufficiency and respiratory failure (WO/EP97/06225, 1999), and also of asthma (U.S. Pat. No. 6,093,746, 2000). The use of Creatine phosphate is shown for the treatment of cardiovascular diseases, promising for the treatment of new-growth tissue (U.S. Pat. No. 5,219,846, 1993).

At the same time the use of Creatine and Creatine phosphate is limited because of poor solubility and instability in aqueous media at physiological pH-values (RU 2295261, 2007). Moreover, Creatine is poorly absorbed from the gastrointestinal tract; the absorption degree is 1÷14%. This requires high usage doses of Creatine. For the effective use of Creatine, compositions produced at the present time require consumption in an amount up to 20 g per day. At the same time, besides increasing the therapy cost, administering high doses of Creatine may lead to negative consequences for the organism, such as disturbance of nitrogen exchange, gastrointestinal disorders, diarrhea, etc.

Therefore preparation of Creatine derivatives possessing a greater stability or higher biological activity represents a big interest that allows, on the one hand, reducing the dose of administered substance and, on the other hand, finding new fields of application therefor.

Derivatives of Creatine and different organic acids have attracted the greatest interest. There is known the use of Creatine pyruvates (U.S. Pat. No. 6,166,249, 2000; RU 2 114 823, 1998) for increasing the workability, for reduction of the body weight, for adaptation to oxygen deficiency conditions at ischemia, the use as a food additive, for skin protection against ageing and sun affection (U.S. Pat. No. 7,186,754, 2007), in the treatment of female sexual disorders, in particular, dysmenorrhea (U.S. Pat. No. 6,503,951, 2000).

The derivatives of Creatine and malonic, maleinic, fumaric, orotic acids and taurine (CN 10/249,338, 2003; U.S. Pat. No. 6,861,554, 2005; U.S. Pat. No. 6,166,249, 2000; CN 10/740,263, 2003) are indicated for medical nutrition as food additives; Creatine citrate (US 2004/077719, 2004) is recommended as a nootropic agent, as well as for using in cosmetic compositions. Among other Creatine derivatives, a magnesium salt of Creatine phosphate (CN 1709896, 2005) should be noted, which salt is indicated for the cardiac muscle.

The most similar to the claimed substances are Creatine esters, such as ethyl and benzyl esters (WO 02/22135, 2002), and compositions on their basis, which have a higher solubility in water and better permeability through the cell membrane in comparison with Creatine. Efficiency of the Creatine esters wasn't examined. However, it was assumed that the aforesaid derivatives being transferred into blood, and being acted upon by enzymes (esterases), are converted into Creatine. Preparations based on the Creatine esters are used as a food additive per os in the form of solutions, emulsions, pills, and capsules.

A disadvantage of the aforesaid compounds is their insufficient stability in the organism and low bioequivalence. It makes the use of Creatine esters in the solid forms or powders and in increased doses per day preferable.

At the present time, there is known a numerous group of drugs, capable of affecting the energy metabolism of the brain tissue, specifically, of activating the integrative functions of brain, and of the brain stability with regard to damaging factors. (M. D. Mashkovsky. Medications. M., Medicine; Goodman E. Gilman's. The Pharmacological Basis of Therapeutics, 11 ed, McGraw-Hill, Medical Publishing Division, New York 2006; RU 1 746 886, 1991, WO96/08527, 1996). In particular, the drug group includes: pyrrolidone derivatives (f.e., pyracetam) activating the energy exchange; drugs enhancing the cholinergic processes (f.e., amyridine, tacrine, glyatiline etc.; GABA-energy drugs (f.e., γ-aminobutyric acid, hopantenic acid, pycamylon, phenybut), activating enzymes of the Krebs cycle; antioxidants and membrane-protectors (f.e., mexidol, meclophenoxate, piritino, ubiquinone); drugs of a complex metabolic action (f.e., vinpocetine) optimizing the oxidation-reduction processes, enhancing of the energy metabolism.

The disadvantages the most of aforesaid substances are: a narrow spectrum of action associated with a considerable number of contra-indications, and moderate neuroprotective efficiency. At the same time, it's known that the clinical using of effective neuroprotectors would allow increasing the share of "small" strokes among ischemic damages in the cerebral blood flow, reducing the infarction zone sizes considerably, extending the period of "therapeutic window and protecting from the reperfusion injuries (Lancet, 2004, 363, 349-45).

Among of this drugs group, Actovegine is of the widest use, which drug is the nearest prior art substance to the claimed compounds with regard to its action. Actovegin contains deproteinized hemoderivative extracted from calf blood, used in the form of pills or solution for injections (Guide VIDAL, 2001, AstraPharmService, p. B-18).

OBJECT AND BRIEF DESCRIPTION OF THE INVENTION

Therefore, a primary object of the present invention is the obtaining of novel Creatine derivatives produced through chemical synthesis, which derivatives should possess a higher stability and a wider spectrum of biological actions, in particular, the neuro-protective activity. Another object of the present invention may become apparent for one skilled in the art upon learning the present disclosure.

According to preferred embodiments of the invention, novel substances (compounds) are prepared through interaction of guanidinylating agents with sarcosine amides of amino acids or their derivatives in polar organic solvents at a temperature not exceeding 50° C. The compounds can be used as remedy having the neuroprotective activity.

DETAIL DESCRIPTION OF THE INVENTION

While the invention may be susceptible to embodiment in different forms, there are shown in the drawings, and will be described in detail herein, specific embodiments of the present invention, with the understanding that the present disclosure is to be considered an exemplification of the principles of the invention, and is not intended to limit the invention to that as illustrated and described herein.

The above stated object has been achieved in the present invention by providing synthesis and using of Creatine derivatives having a general formula of NH=C(NH$_2$)—N(CH$_3$)—CH$_2$—CO—NH—R*X, wherein: R is amino acid residue or substituted amino acid residue; X is lower-molecular-weight organic acid, or mineral acid, or water.

The aforementioned amino acids can be represented by: various aliphatic, aromatic, and heteroaromatic L-amino acids, or their derivatives, in particular, esters of amino acids, amino acids amides, peptides etc. The aforementioned organic or mineral acids can be represented by: pharmaceutically acceptable lower organic or mineral acids (molecular weight usually less than 300) such as acetic, hydrochloric, citric acids, etc.

As it was determined during biological experiments, synthesized amides of Creatine have an enhanced solubility and stability in aqueous solutions in comparison with well-known analogues that allows deploying them more widely as a source of Creatine in the organism.

In preferred embodiments, Creatine amides can be prepared by interaction of amides of sarcosine having a general formula of HN(CH$_3$)—CH$_2$—CO—NH—R*X, wherein: R is amino acid residue or substituted amino acid residue; X is low-molecular-weight organic acid or mineral acid or water with de-protected or protected guanidinylating agents with sarcosine amides in polar organic solvents at a temperature not exceeding 50° C. Carrying out the synthesis at a higher temperature usually reduces the yield of desired product and negatively affects its biological activity due to side reactions. The choice of specific synthesis conditions is determined by properties of reagents and the desired product.

Amino acids derivatives and amides of sarcosine, can be prepared in particular by using standard chemical reactions of peptides chemistry, described in literature (e.g. A. A. Gershkovich, B. K. Kibirev « Synthesis of peptides. Reagents and methods» . Kiev. « Naukova dumka» . 1987) or by using a raw material in the form of amides of Creatine, prepared by the method mentioned above.

Amino acids derivatives and amides of sarcosine, can be prepared in particular by using standard chemical reactions of peptides chemistry, described in literature (e.g. A. A. Gershkovich, B. K. Kibirev « Synthesis of peptides. Reagents and methods» . Kiev. « Naukova dumka» . 1987) or by using a raw material in the form of amides of Creatine, prepared by the method mentioned above. The analysis conditions were: UV-detection at 230 nm, gradient elution in the system 0.1% aqueous solution of trifluoroacetic acid—acetonitrile at the flow rate 1 ml/min—for analytical chromatography, and gradient elution in the system 0.1% aqueous solution of trifluoroacetic acid—acetonitrile at the flow rate 5 ml/min—for semi-preparative chromatography. The mass-spectra were run on the time-of-flight mass-reflectrone MX-5303 with the ions source of the "Electrospray" type (Division of the Institute of Energy Problems in Chemical Physics of the Russian Academy of Sciences).

The most perspective field of utilization of Creatine amides is their application as substances possessing a neuroprotective activity. As it was shown in the aforementioned experiments, administering the Creatine amides to an organism at a dose of 20 mg/kg and more, the enhancing of cognitive functions was observed that makes Creatine amides perspective remedies for prevention and therapy of ischemic brain damages.

Creatine amides can be administered into the organism independently and within compositions, containing a mixture of an active ingredient with auxiliary components. The auxiliary components are substances permitted by the Pharmacopoeia; they enhance the conditions of preparation, storage, or administering the remedy, for instance: solvents, excipients, adhesive agents, aerating agents, sliding-lubricating substances, film-formators, pigments, plasticizers, prolongating agents, aromatizers, flavor additives, stabilizers, preservatives, etc.

Exemplarily, the auxiliary substances may include: solvents, such as water; solutions of potassium, magnesium, zinc, manganese salts, saline, syrup masses; excipients, such as crospovidone, sugars and their derivatives, polysaccharides and their derivatives, in particular, lactose, sucrose, microcrystalline cellulose, starch, glucose, mannitol, cyclodextrins, alginates, dextrine, organic and mineral acids salts; such adhesive agents as water, ethyl alcohol, sugar syrup, starch glue, the solutions of cellulose derivatives, povidones, gelatine, alginates etc.; such aerating agents as starches, crospovidones, polysorbates, sodium lauryl sulfate, aerosil etc.; sliding-lubricating substances, such as starches, talc, polyethylene glycol, aerosil, calcium and magnesium stearates, stearic acid, sodium stearylfumarate etc.; film-formators such as alkylcelluloses and their derivatives etc.; plasticizers such as polysorbates, glycerine, polyethylene glycol, propylene glycol, dibutylphthalate, glycerine triacetate, etc.

The following examples illustrate the invention.

Example 1

Synthesis of Creatinyl-γ-Aminobutyric Acid Ethyl Ester Acetate 0.94 ml (4.16 mM) of N,N-diisopropylethylamine and 0.9 g (2.08 mM) of benzotriazole-1-carboxamidinium tosylate were added to the solution of 0.66 g (2.08 mM) of sarcosyl-γ-aminobutyric acid ethyl ester trifluoroacetate in 1.5 ml of N,N-dimethylformamide. The reaction mixture was stirred for 60 hours at the room temperature, then diluted with n-butyl alcohol and water, the solvent was evaporated. The residue was recrystallized from isopropyl alcohol and purified by ion exchanged chromatography on the column with Sephadex SE C-25 in 0.002 M pyridine-acetate buffer. The fractions containing the desired product were combined and the solvent was evaporated. Yield: $C_{10}H_{20}N_4O_3*CH_3COOH$ 0.3 g (59%). MS, found: m/z: 245.17. Calculated: M 244.15.

Example 2

Synthesis of Creatinyl-L-Phenylalanine Amide Hydrate 3.2 ml (22.9 mM) of triethylamine and 5.3 g (11.45 mM) of N,N-dibenzyloxycarbonyl-1-H-benzotriazole-1-carboxamidine were added to the solution of 4 g (11.45 mM) sarcosyl-L-phenylalanine amide trifluoroacetate in 30 ml of N,N-dimethylformamide. The reaction mixture was stirred for 20 hours at the room temperature and diluted with 200 ml of ethylacetate. The organic phase was washed with 5% solution of $NaHCO_3$, water, 1N HCl, water and kept for 12 hours at (+)4° C. The so formed residue, containing dibenzyloxycarbonyl-creatinyl-L-phenylalanine amide was filtered, washed with cold ethylacetate and dried in vacuo. Yield: 3.8 g (62%).

For removal of the protecting group, 3.8 g (6.96 mM) of dibenzyloxycarbonyl-creatinyl-phenylalanine amide was dissolved in 150 ml of the mixture of 1,4-dioxane-water (9:1) and hydrogenated over Pd black for 5 hours (controlled by thin-layer chromatography). The catalyst was filtered, the solvent was evaporated, and the residue containing creatinyl-L-phenylalanine amide hydrate was crystallized from isopropyl alcohol. Yield: $C_{13}H_{19}N_5O_2*H_2O$ 1.2 g (43%). MS, found: m/z: 278.15. Calculated: M 277.15.

Example 3

Synthesis of Creatinyl-L-Phenylalanine Amide Acetate

Creatinyl-L-phenylalanine amide prepared according to the example 2 was dissolved in water and applied on the column 25×100 mm with a silica gel Lichroprep RP-18 (43-60 μm, Merck) then eluted by 0.2% acetic acid and separated from the solution. Yield: $C_{13}H_{19}N_5O_2*CH_3COOH$ 0.72 g (60%). MS, found: m/z: 278.15. Calculated: M 277.15.

Example 4

Synthesis of Creatinyl-Glycine Benzyl Ester Hydrochloride 1.97 ml (14.14 mM) of triethylamine and 2.8 g (7.07 mM) of N,N-di-tert-butyloxycarbonyl-1-H-benzotriazole-1-carboxamidine were added to the solution of 2.5 g (7.07 mM) of sarcosyl-glycine benzyl ester trifluoracetate in 20 ml of N,N-dimethylformamide, and stirred for 24 hours at 20° C. The reaction mixture was diluted with 200 ml of ethylacetate, the organic phase was washed with 5% solution of $NaHCO_3$, 1N $H_2SO_4$, water and dried over $Na_2SO_4$. The solvent was evaporated in the rotary evaporator and the residue was crystallized from the mixture diethyl ether-petroleum ether. Yield of di-tert-butyloxycarbonyl-creatinyl-glycine benzyl ester 2.3 g (67%). $R_f$ 0.68 (B).

For removal of the protecting groups a stream of HCl dry was bubbled through the solution containing 2.3 g (4.78 mM) of di-tert-butyl-oxycarbonyl-creatinyl-glycine benzyl ester in 70 ml of dry diethyl ether at 0° C. and strongly stirred for 45 min. The solid formed was filtered, washed with dry diethyl ether and dried over NaOH in the dessicator. Yield: $C_{13}H_{18}N_4O_3$—0.3 g (20%). MS, found: m/z: 279.14 Calculated: M 278.14.

Example 5

Synthesis of Creatinyl-Tyrosine Amide Succinate

The solution of dicyclohexylcarbodiimide (4.9 g, 23.74 mM) in 10 ml of N,N-dimethylformamide was added to the solution of tert-butyloxycarbonyl-sarcosine (4.49 g, 23.74 mM) and hydroxybenzotriazole (3.21 g, 23.74 mM) in 30 ml of N,N dimethylformamide at cooling on the ice bath and stirring. Tyrosine methyl ester hydrochloride (5 g, 21.58 mM) and triethylamine (3.02 ml, 21.58 mM) were added to the reaction mixture in 10 minutes, then stirred for 1 hour at 0° C. and 12 hours at 20° C. The reaction mixture was diluted with 300 ml of ethylacetate, washed with 5% of $NaHCO_3$, 1N $H_2SO_4$, water and dried up $Na_2SO_4$. The solvent was evaporated on the rotary evaporator. $R_f$ of the desired product: 0.75 in the system $CHCl_3$-EtOAc-MeOH (20:10:3). A yield of tert-butyloxycarbonyl-sarcosyl-tyrosine methyl ester was 6.2 g (78.5%).

6.2 g (16.92 mM) of tert-butyloxycarbonyl-sarcosyl-tyrosine methyl ester was dissolved in a flask with 200 ml 6 M solution of ammonia in methanol cooled down to 0° C. The flask was tightly closed and the solution was kept for 48 hours at the room temperature. The reaction pathway control was carried out by thin-layer chromatography in the system $CHCl_3$:EtOAc:MeOH (20:10:3) ($R_f$ of the product: 0.32). The solvent was evaporated, the residue was triturated with diethyl ether until a dry amorphous solid formation and dried in vacuo. Yield of tert-butyl-oxycarbonyl-sarcosyl-tyrosine amide: 5.4 g (90%).

5.4 g of tert-butyloxycarbonyl-sarcosyl-tyrosine amide was dissolved in 20 ml of trifluoroacetic acid, kept for 15 min at the room temperature, the solvent was evaporated in a rotary evaporator at 25° C. The residue was crystallized from diethyl ether and dried up in vacuum. The purity of the obtained product was verified by reversed phase HPLC on the column Luna C-18 4.6×150 mm, 5 μm (Phenomenex) using the linear gradient of acetonitrile in water containing 0.1% of ortho-phosphoric acid (0÷20% of acetonitrile in 20 min); the flow rate 1 ml/min. A yield of sarcosyl-tyrosine amide trifluoracetate was 5.4 g (96%).

N,N'-dimethylformamide N,N-diisopropylethyl amine (5.06 ml, 29.6 mM) was added to the solution of sarcosyl-tyrosine amide trifluoracetate (5.4 g, 14.8 mM) and benzotriazole-1-carboxamide tosylate (4.92 g, 14.8 mM) in 7 ml at stirring. According to HPLC data a completion of the reaction pathway was about 90% in 72 hours. The solvent was evaporated with a mixture of water: n-butanol (2:3), the residue was dissolved in 20 ml of water, applied on the column 25×150 mm with Sephadex SE C-25 (Pharmacia Fine Chemicals), adjusted in 0.002 M pyridine-succinate buffer. The flow rate was 2 ml/min. The further separation was carried out in the gradient of pyridine-succinate buffer in the concentration range from 0.002 to 0.5 M. The fractions containing creatinyl-tyrosine amide succinate were analyzed by Reverse Phase HPLC, combined and evaporated. The final purification was carried out by crystallization from isopropyl alcohol. The purity of the obtained product was verified by Reversed Phase HPLC on the column Luna C-18 4.6×150 mm, 5 μm (Phenomenex) using the linear gradient of acetonitrile in the water containing 0.1% of ortho-phosphoric acid (0÷20% of acetonitrile in 20 min), the flow rate 1 ml/min. A yield of creatinyl-tyrosine amide succinate was 2.7 g (51%). MS, found: m/z: 292.27. Calculated: M 292.29.

Example 6

Synthesis of Creatinyl-Glycine Ethylamide Acetate 10 ml of ethylamine was added to the solution of tert-butyloxycarbonyl-sarcosyl-glycine methyl ester (15 g, 54.88 mM) in 20 ml of dry ethanol in a flask, cooled down to 0° C., the flask was tightly closed and kept at the room temperature. According to TLC data, the reaction was completed in 48 hours. The solvent was evaporated on the rotary evaporator. $R_f$ of the product: 0.45 in the system $CHCl_3$:EtOAc:MeOH (20:10:3). A yield of tert-butyloxycarbonyl-sarcosyl-glycine ethylamide—14.7 g (98%).

14.7 g (53.85 mM) of tert-butyloxycarbonyl-sarcosyl-glycine ethylamide was dissolved in 40 ml of trifluoroacetic acid, kept for 15 min at room temperature, the solvent was evaporated on the rotary evaporator at 25° C. The residue was crystallized from 150 ml of diethyl ether and dried up in vacuum. The purity of the obtained product was controlled by Reversed Phase HPLC on the column Zorbax ODS 250×4.6 mm, 5 μm (DuPont) in the mobile phase containing 0.1% of TFA (0.5÷20% of acetonitrile in 20 min). Yield of sarcosyl-glycine ethyl amide trifluoracetate: 13.9 g (92%).

6 ml (34.6 mM) of N,N-diisopropylethylamine was added to the solution of sarcosyl-glycine ethylamide trifluoracetate (5 g, 17.3 mM) and benzotriazole-1-carboxamidinium tosylate (5.78 g, 17.3 mM) in 10 ml of N,N-dimethylformamide at stirring. According to the Reversed Phase HPLC data on the column Zorbax ODS 250×4.6 mm, 5 μm (gradient of acetonitrile 0÷20% in 20 minutes) the reaction was completed at 90% in 48 hours. The solvent was evaporated with the mixture water-n-butanol (2:3), the residue was dissolved in 40 ml of 20% isopropyl alcohol in water and applied on the column 25×150 mm with Sephadex SE C-25 (Pharmacia Fine Chemicals), adjusted in 0.002 M pyridine-acetate buffer containing 20% of isopropyl alcohol. Further, the separation was carried out under a gradient of the buffer concentration from 0.002 to 0.25 M. The fractions containing creatinyl-glycine ethylamide acetate were analyzed by the Reversed Phase HPLC on the column Zorbax ODS 250×4.6 mm, 5 μm in the mobile phase containing 0.1% of TFA (0÷20% of acetonitrile in 20 minutes), combined and evaporated. The final purification of the product was carried out by crystallization from 10 ml of isopropyl alcohol at (−)5° C. The purity of the product was controlled by the Reversed Phase HPLC on the column Zorbax ODS 250×4.6 mm, 5 μm (DuPont) in the mobile phase containing 0.1% of TFA (0.5÷20% of acetonitrile in 20 min). A yield of creatinyl-glycine ethylamide acetate was 2.7 g (56%). MS, found: m/z: 214.27. Calculated: M 214.25.

Example 7

Synthesis of Creatinyl-Phenylalanyl-Arginyl-Glycine Ethyl Ester Acetate

The solution of N,N-dicyclohexylcarbodiimide (4.44 g, 21.52 mM) in 10 ml of N,N-dimethylformamide was added To the solution $N^\alpha$-benzyloxycarbonyl, $N^\delta$-tert-butyloxycarbonyl-ornithine (7.9 g, 21.52 mM) and hydroxybenzotriazole (2.91 g, 21.52 mM) in 20 ml of N,N-dimethylformamide at cooling on the ice bath and stirring. Glycine ethyl ester hydrochloride (3 g, 21.52 mM) and triethylamine (3 ml, 21.52 mM) were added in 10 min to the reaction mixture, stirred for 1 hour at 0° C. and 20 hours at 20° C. The reaction mixture was diluted with 300 ml of ethylacetate, washed with 5% solution of $NaHCO_3$, 1N $H_2SO_4$, water and dried up over $Na_2SO_4$. The solvent was evaporated on the rotary evaporator, the residue—crystal substance. M.p. 113-115° C.; $R_f$ 0.89 in the system $CHCl_3$:EtOAc:MeOH (20:10:3). A yield of $N^\alpha$-benzyloxycarbonyl, $N^\delta$-tert-butyloxycarbonyl-ornithyl-glycine ethyl ester was 8.6 g (88%).

Palladium black was added to the solution of 8.6 g $N^\alpha$-benzyloxycarbonyl, $N^\delta$-tert-butyloxycarbonyl-ornithyl-glycine ethyl ester in 150 ml of methanol distilled over Mg, and hydrogenated for 3 hours. The completion of the reaction was controlled by TLC in the system $CHCl_3$:EtOAc:MeOH (20: 10:3). The solvent was evaporated on the rotary evaporator. The purity of the obtained product was verified by TLC in the system EtOAc:n-BuOH:AcOH:$H_2O$ (2:1:1:1) ($R_f$ 0.43). A yield of $N^\delta$-tert-butyloxycarbonyl-ornithyl-glycine ethyl ester was 6 g (100%).

The solution of dicyclohexylcarbodiimide (4.3 g, 20.86 mM) in 10 ml of N,N-dimethylformamide was added to the solution of $N^\alpha$-benzyloxycarbonyl-phenylalanine (6.24 g, 20.86 mM) and hydroxybenzotriazole (2.82 g, 20.86 mM) in 20 ml of N,N-dimethylformamide at cooling on the ice bath and stirring $N^\delta$-tert-butyloxycarbonyl-ornithyl-glycine ethyl ester (6 g, 18.92 mM) was added to the reaction mixture in 10 min, stirred for 1 hour at 0° C. and 20 hours at 20° C. The reaction mixture was diluted with 300 ml of ethylacetate, washed with 5% solution of $NaHCO_3$, 1N $H_2SO_4$, water and dried over $Na_2SO_4$. The solvent was evaporated on the rotary evaporator, the product crystallized upon evaporation. M.p. 179-182° C.; $R_f$ 0.52 in the system $CHCl_3$:EtOAc: MeOH (20:10:3). A yield of $N^\alpha$-benzyloxycarbonyl-phenylalanyl-$N^\delta$-tert-butyloxycarbonyl-ornithyl-glycine ethyl ester was 8.7 g (77%).

Palladium black was added to the solution of 8.7 g of $N^\alpha$-benzyloxycarbonyl-phenylalanyl-$N^\delta$-tert-butyloxycarbonyl-ornithyl-glycine ethyl ester in 150 ml of methanol distilled over Mg, and hydrogenated for 3 hours. The completion of the reaction was controlled by TLC in the system $CHCl_3$-EtOAc-MeOH (20:10:3). The solvent was evaporated on the rotary evaporator. The purity of the obtained product was verified by TLC in the system EtOAc:n-BuOH:AcOH:$H_2O$ (2:1:1:1) ($R_f$ 0.27). A yield of phenylalanyl-$N^\delta$-tert-butyloxycarbonyl-ornithyl-glycine ethyl ester was 6.58 g (100%).

The solution of dicyclohexylcarbodiimide (4.12 g, 20.00 mM) in 10 ml of N,N-dimethylformamide was added to the solution of tert-butyloxycarbonyl-sacrosine (3.78 g, 20 mM) and hydroxybenzotriazole (2.7 g, 20.00 mM) in 20 ml of N,N-dimethylformamide at cooling on the ice bath and stirring. Phenylalanyl-$N^\delta$-tert-butyloxycarbonyl-ornithyl-glycine ethyl ester (6.58 g, 14.2 mM) was then added in 10 min to the reaction mixture and stirred for 1 hour at 0° C. and 20 hours at 20° C. The reaction mixture was diluted with 300 ml of ethylacetate, washed with 5% solution of $NaHCO_3$, 1N $H_2SO_4$, water. The solution was cooled down and kept for 3 hours at (+) 4° C.; the product was formed as a solid. The solid was filtered, washed with ether and dried in vacuum. M.p. 189-192° C.; $R_f$ 0.40 in the system $CHCl_3$:EtOAc:MeOH—(20:10:3). A yield of tert-butyl-oxycarbonyl-sacrosyl-phenylalanyl-$N^\delta$-tert-butyloxycarbonyl-ornithyl-glycine ethyl ester was 6.5. g (72%).

6.5 g of tert-butyl-oxycarbonyl-sacrosyl-phenylalanyl-$N^\delta$-tert-butyloxycarbonyl-ornithyl-glycine ethyl ester was dissolved in 40 ml of trifluoroacetic acid, kept for 15 min at room temperature, the solvent was evaporated on the rotary evaporator at 25° C. The residue was crystallized from 250 ml of diethyl ether and dried in vacuo. The purity of the obtained product was verified by the Reversed Phase HPLC on the column Phenomenex Luna C-18, 5μ, 4.6×150 mm using the linear gradient of acetonitrile in the water, containing 0.1% of trifluoroacetic acid (7÷27% of acetonitrile in 20 min), the flow rate was 1 ml/min. A yield of sarcosyl-phenylalanyl-ornithyl-glycine ethyl ester trifluoracetate—6.5 g (96%).

The solution of sarcosyl-phenylalanyl-ornithyl-glycine ethyl ester trifluoroacetate (2 g, 3.02 mM) in 5 ml of water was applied on the column 15×100 mm with Amberlite IRA-67 ("Sigma") in OH⁻ form, the column was eluted with water. The fractions with pH more than 7 were combined, evaporated and dried by triple distillation with isopropyl alcohol. The obtained sarcosyl-phenylalanyl-ornithyl-glycine ethyl ester was dissolved in 5 ml of N,N-dimethylformamide, 0.5 g of LiCl (Merck) was added to improve of solubility then N,N-diisopropylethylamine (1.05 ml, 6.04 mM) and benzotriazole-1-carboxamidinium tosylate (2.01 g, 6.04 mM) were added, 5 ml of N,N-dimethylformamide was added and stirred for 72 hours. According to the Reversed Phase HPLC data on the column Phenomenex Luna C-18, 5μ, 4.6×150 mm, the linear gradient of acetonitrile in the water, containing 0.1% of trifluoroacetic acid (7÷27% of acetonitrile in 20 min, the flow rate 1 ml/min), the reaction was completed by more than 90% in 40 hours. The solvent was evaporated with the mixture water—n-butanol (2:3), the residue was dissolved in 20 ml of water and applied on the column 25×150 mm with Sephadex SE C-25 (Pharmacia Fine Chemicals), adjusted in 0.002 M pyridine-acetate buffer. The column was eluted with 400 ml of 0.002 M buffer (the flow rate was 2 ml/min), separation was carried out in a gradient of 0.002÷0.5 M of pyridine-acetate buffer. The fractions containing creatinyl-phenylalanyl-arginyl-glycine ethyl ester acetate were combined and evaporated. The final purification of the product was carried out by crystallization from 20 ml of isopropyl alcohol at the room temperature. The purity of the obtained product was verified by the Reversed Phase HPLC on the column Luna C-18, 5 μM, 4.6×150 mm (Phenomenex) using the linear gradient of acetonitrile in the water containing 0.1% of orthophosphoric acid (8÷28% of acetonitrile in 20 min); the flow rate was 1 ml/min. A yield of creatinyl-phenylalanyl-arginyl-glycine ethyl ester acetate was 0.72 g (37%). MS, found: m/z: 520.60. Calculated: M 520.61.

Example 8

Synthesis of Creatinyl-Phenylalanine hydrochloride

The solution of dicyclohexylcarbodiimide (4.36 g, 21.14 mM) in 10 ml of N,N-dimethylformamide was added to the solution of tert-butyl-oxycarbonyl-sarcosine (4 g, 21.14 mM) and hydroxybenzotriazole (2.86 g, 21.14 mM) in 30 ml of N,N-dimethylformamide at cooling on the ice bath and stirring. Phenylalanine benzyl ester p-toluenesulfonic acid (8.13 g, 19.03 mM) and triethylamine (2.7 ml, 19.03 mM) were added in 10 min to the reaction mixture, stirred for 1 hour at 0° C. and 20 hours at 20° C. N,N-dicyclohexylurea was filtered, the reaction mixture was diluted with 200 ml of ethylacetate, washed with 5% solution of $NaHCO_3$, 1N $H_2SO_4$, water and dried up over $Na_2SO_4$. The solvent was evaporated on the rotary evaporator. $R_f$ of desired substance: 0.85 in the system $CHCl_3$:EtOAc:MeOH (20:10:3). A yield of tert-butyl-oxycarbonyl-sarcosyl-phenylalanine benzyl ester was 7.3 g (90%).

7.3 g (17.15 mM) of tert-butyl-oxycarbonyl-sarcosyl-phenylalanine benzyl ester was dissolved in 20 ml of 65% trifluoroacetic acid in $CH_2Cl_2$, kept for 30 min at room temperature, the solvent was evaporated on the rotary evaporator at 25° C. The residue was crystallized from 200 ml of diethyl ether, dried in vacuo. The purity of the obtained product was verified by Reversed Phase HPLC on the column Phenomenex Luna C-18, 5 μM, 4.6×150 mm (20÷40% of acetonitrile in 20 min). A yield of sarcosyl-phenylalanine benzyl ester trifluoracetate was 6 g (80%).

N,N'-diisopropylethylamine (4.74 ml, 27.24 mM) was added to the solution of sarcosyl-phenylalanine benzyl ester trifluoracetate (6 g, 13.62 mM) and benzotriazole-1-carboxamidinium tosylate (4.54 g, 13.62 mM) in 7 ml of N,N'-dimethylformamide at stirring. According to the Reversed Phase HPLC data on the column Phenomenex Luna C-18, 5 μM, 4.6×150 mm (20÷40% of acetonitrile in 20 minute) the reaction was completed in 72 hours. The solvent was evaporated with a mixture of water-n-butanol (2:3), the residue was dissolved in 80 ml of 30% aqueous isopropyl alcohol and applied on the column 25×150 mm with Sephadex SE C-25 (Pharmacia Fine Chemicals), adjusted in 0.002 M pyridine-acetate buffer containing 20% of isopropyl alcohol. The column was eluted with 400 ml of the starting buffer (the flow rate was 2 ml/min), the separation was carried out in the gradient of 0.002÷0.5 M of pyridine-acetate buffer containing 20% of isopropyl alcohol.

The fractions containing AcOH*Cr-Phe-OBzl were analyzed by Reversed Phase HPLC on the column Phenomenex Luna C-18, 5 μM, 4.6×150 mm (20÷40% of acetonitrile in 20 min) were combined and evaporated. A yield of creatinyl-phenylalanine benzyl ester acetate was 2.54 g (41%).

Then, 2.54 g (5.93 mM) of creatinyl-phenylalanine benzyl ester acetate was dissolved in 80 ml of methanol and hydrogenated over palladium black. During the reaction, the product was deposited as a solid. According to TLC data, in the system of ACN-H$_2$O—AcOH (7:1:1), hydrogenation was completed in 4 hours. The solid formed together with the catalyst were filtered, washed with methanol and dissolved in 200 ml of 0.01 M HCl in 40% aqueous methanol. The catalyst was filtered, the filtrate was evaporated, the resultant residue was crystallized from 10 ml of isopropyl alcohol. The purity of the obtained product was verified by the Reversed Phase HPLC on the column Luna C-18, 5 μM, 4.6×150 mm, Phenomenex (5÷25% of acetonitrile in 20 min). A yield was 1.1 g (69%). MS, found: m/z: 278.27. Calculated: M 278.29.

Example 9

Study of the Amides of Creatine Stability in Aqueous Solution and Blood Plasma

Study of the Creatine derivatives stability in aqueous solution, as well as in human and rat blood plasma was carried out by the method of Reversed Phase HPLC using a chromatography system, known as Beckman System Gold™ (USA) in the following configuration: Programmable Solvent Module 126, Manual Injector Rheodyne 7725i, Programmable Detector Module 166, featured with the Beckman System Gold Chromatography Software™. The analysis was carried out on the column Luna 5μ C18(2) 100 Å 150×4.6 mm (Phenomenex, USA) with the precolumn Guard Cartridge C18 at the flow rate 1 ml/min in the linear gradient of acetonitrile: for analogue from the Example 1 from 5 to 25% of acetonitrile in 20 min (A: 0.1% of H$_3$H$_2$O$_4$—H$_2$O, B: 0.1% of H$_3$PO$_4$-acetonitrile), in case of substance from the Examples 2÷8: from 3 to 23% of acetonitrile in 20 minutes. The detection was carried out on the wave length 220 nm. The samples dosing on the column was carried out by the loop 20 μl.

For preparation of the examined substances solutions, a proximate batch of each peptide was taken on the analytical scales. The calculated volume of double-distilled water was added to that batch to achieve a concentration of 2 mg/ml. A portion of the solution was diluted to 10 times, and analysis of the sample was carried out immediately. Further this solution was kept at the room temperature and the analysis was repeated in 3 hours. According to the results of estimations, the peaks area of both samples reduces insignificantly (less than 3%) in 3 hours; any appearance of the new peaks wasn't detected.

For the study of Creatine amides stability, 1 ml of water or blood plasma was added to 200 μl of aqueous solution of starting amide with a concentration of 2÷3 mg/ml then shaken; a probe volume of 200 μl was taken up immediately and analysis of an initial concentration of the Creatine amide was carried out. Further, the solution was placed into a vibrothermostat at a temperature of 37° C., then aliquote 200 μl was taken up in 0.5, 1, and 3 hours of thermostatics. 20 μl 10% solution of trichloroacetic acid was added to the taken probe, and kept for 15 min at temperature (−)24° C., then centrifuged at 6000×g for 5 minutes for sedimentation of plasma proteins, supernatant was taken up and its analysis was carried out.

For evaluation of samples' stability, peak areas of a corresponding compound at the beginning of experiment and at selected time intervals were compared (Tables 1, 2).

TABLE 1

Stability of the Creatine analogues in human blood plasma.

| Sample | Stability in human blood plasma | | | | |
|---|---|---|---|---|---|
| | 0 h | 0.5 h | 0.75 h | 1 h | 3 h |
| Example 1 | 100% | 99% | — | 103% | 104% |
| Example 2 | 100% | 99% | — | 99% | 100% |
| Example 3 | 100% | 100% | — | 100% | 100% |
| Example 4 | 100% | 98% | — | 100% | 99% |
| Example 5 | 100% | 98% | — | 97% | 93% |
| Example 6 | 100% | 97% | — | 95% | 95% |
| Example 7 | 100% | 94% | — | 90% | 85% |
| Example 8 | 100% | 99% | — | 98% | 97% |
| Creatine benzyl ester | 100% | — | 53% | — | 46% |

TABLE 2

Creatine analogues stability in a rat blood plasma

| Sample | Stability in a rat blood plasma | | | |
|---|---|---|---|---|
| | 0 h | 0.5 h | 1 h | 3 h |
| Example 1 | 100% | 96% | 98% | 99% |
| Example 2 | 100% | 100% | 97% | 98% |
| Example 3 | 100% | 96% | 98% | 99% |
| Example 4 | 100% | 99% | 99% | 96% |
| Example 5 | 100% | 98% | 97% | 93% |
| Example 6 | 100% | 97% | 97% | 95% |
| Example 7 | 100% | 93% | 92% | 85% |
| Example 8 | 100% | 98% | 98% | 95% |

As it follows from the presented data, Creatine amides have a high stability in the human and rat blood plasma: their concentration remained invariable during 3 hours, whereas the reference substance (Creatine benzyl ester) concentration in human blood plasma during 0.75 hours decreased by 53% in all occasions.

Example 10

Nootropic Activity of Creatine Amides

Study of Creatine amides influence upon their ability to demonstrate a neuroprotective action on the brain tissues, were carried out on the model of focal and global cerebral ischemia in rats. The global cerebral ischemia in male rats S-D anaesthetized with Nembutal was induced by bilateral common carotid artery occlusion for 12 minutes with simultaneous controlled hypotension (45 mmHg). The intracerebral-ventricular (i.c.v.) cannula was introduced stereotactically in the left lateral cerebral ventricle with the use of ketamine anesthesia and connected to the osmotic mini-pump Alzet (AP), (model 1002, solution supplement rate 0.25 μl/h), which was previously filled with the experimental solution and placed subcutaneous between the shoulder bones.

The examined samples were administered intravenous (a, b), or per os (a) in a dose of 20 mg/kg, in the following variants of experiment:

(a)—5 days before ischemia and continuing during 7 days after ischemia (evaluation of the sample efficiency for ischemia prevention and therapy);

(b)—in 30 min after ischemia induction and continuing during 7 days (evaluation of the sample efficiency for ischemia therapy);

(c)—1 hour before ischemia (evaluation of the sample efficiency for ischemia prevention and therapy).

On the 7$^{th}$ day after ischemia, the rats were killed by decapitation, the brain was removed, placed into 2% paraformaldehyde for 12÷24 hours, then—into 96% ethanol, encoded for the blinded analysis, and the morphological examination was carried out. The level of brain damage was evaluated according to a collapsed neurons quantity in different brain regions.

A conclusion regarding to the samples efficiency was drawn on the basis of study of their effect on animals behavioral reactions in Morris watermaze and on the basis of a morphological changes in brain tissue analysis by administration of Creatine amides initiated by global and focal cerebral ischemia.

The data of the behavioral testing in the Morris' water labyrinth (MWM—Morris Water Maze) at intra-peritoneal injection of the composition. The sample compositions with the formula stated below were used for the examination (Table 3):

TABLE 3

Compositions for biological examination:

| No | Name of component | Quantity, g |
|---|---|---|
| | Composition 1. | |
| 1 | Amide of Creatine from the example 1 | 20.0 |
| | Sodium chloride | 9.0 |
| | Nipagin | 1.0 |
| | NaOH 0.1M solution | up to pH 7 |
| | H$_2$O | up to 1 L |
| | Composition 2. | |
| 2 | Amide of Creatine from the example 2 | 10.0 |
| | Magnesium sulfate | 10.0 |
| | Nipagin | 1.0 |
| | NaOH 0.1M solution | up to pH 7.2 |
| | H$_2$O | up to 1 L |
| | Composition 3. | |
| 3 | Amide of Creatine from the example 1 | 30.0 |
| | Succinic acid | 0.5 |
| | Nipagin | 1.0 |
| | KOH 0.1M solution | up to pH 7.2 |
| | H$_2$O | up to 1 L |
| | Composition 4 | |
| 4 | Amide of Creatine from the example 3 | 0.35 |
| | Microcrystalline cellulose | 0.0769 |
| | Crospovidone | 0.022 |
| | Calcium phosphate dihydrate | 0.1000 |
| | Sodium stearyl fumarate | 0.1000 |
| | Total: | 0.65 |
| | Composition 5 | |
| 5 | Amide of Creatine from the example 4 | 0.35 |
| | Crospovidone | 0.017 |
| | Lactose | 0.003 |
| | Stearic acid | 0.002 |
| | Potassium citrate | 0.002 |
| | Aerosil | 0.001 |
| | Total: | 0.375 |
| | Composition 6 | |
| 6 | Amide of Creatine from the example 4 | 0.35 |
| | Mannitol | 0.006 |
| | Aerosil | 0.001 |
| | Total: | 0.357 g |

TABLE 3-continued

Compositions for biological examination:

| No | Name of component | Quantity, g |
|---|---|---|
| | Composition 7 | |
| 7 | Actovegin (reference agent) | 0.35 |
| | Microcrystalline cellulose | 0.0769 |
| | Crospovidone | 0.022 |
| | Calcium phosphate dihydrate | 0.100 |
| | Sodium stearyl fumarate | 0.100 |
| | Total: | 0.65 |
| | Composition 8 | |
| 8 | Amide of Creatine from the example 5 | 2.0 |
| | Sodium chloride | 9.0 |
| | Nipagin | 1.0 |
| | NaOH 0.1M solution | up to pH 7.2 |
| | H$_2$O | up to 1 L |
| | Composition 9 | |
| 9 | Amide of Creatine from the example 7 | 2.0 |
| | Sodium chloride | 9.0 |
| | Nipagin | 1.0 |
| | NaOH 0.1M solution | up to pH 7.2 |
| | H$_2$O | up to 1 L |
| | Composition 10 | |
| 10 | Creatine amide from the example 6 | 20.0 |
| | Sodium chloride | 9.0 |
| | Nipagin | 1.0 |
| | NaOH 0.1M solution | up to pH 7.2 |
| | H$_2$O | up to 1 L |

In the process of efficiency analysis concerning a deficit in tissue energy metabolism caused by focal cerebral ischemia (FCI), the data of rats training in MWM groups with intra-peritoneal injections and per os administration of the samples (n=7), of negative control with saline a intra-peritoneal injection (n=13), of positive control (n=5) and false surgery operated animals (FO) (n=5) were compared.

The statistical analysis (the ANOVA method with repeated measurements) showed that the groups were differed substantially in the training course. The training was observed at the experimental group (the samples injection was administered), the positive control group, and the false surgery operated animals. FCI per se blocked the training completely. Rats injected by the sample spent statistically significant less time to find the platform than the rats of negative control rats group in the last two days of training (p<0.02 and p<0.03, respectively; post hoc LSD Fisher test), and weren't differed from the positive control group and the false surgery operated animals (Table 4).

TABLE 4

The data of rats behavioral testing in the Morris Water Maze
Day of training/Time of the platform finding, sec

| 1 | 2 | 3 | 4 | 5 |
|---|---|---|---|---|
| Composition 1, i.e.v. injection, model of experiment a) | | | | |
| 52 ± 5 | 44 ± 3 | 42 ± 3 | 40 ± 2 | 35 ± 3 |
| Composition 2, i.e.v. injection, model of experiment b) | | | | |
| 50 ± 5 | 43 ± 3 | 43 ± 3 | 39 ± 2 | 34 ± 3 |
| Composition 3, i.e.v. injection, model of experiment b) | | | | |
| 47 ± 4 | 45 ± 3 | 41 ± 4 | 39 ± 3 | 35 ± 3 |
| Composition 4, per os, model of experiment a) | | | | |
| 55 ± 3 | 45 ± 5 | 42 ± 3 | 41 ± 3 | 34 ± 4 |

TABLE 4-continued

The data of rats behavioral testing in the Morris Water Maze
Day of training/Time of the platform finding, sec

| 1 | 2 | 3 | 4 | 5 |
|---|---|---|---|---|
| Composition 5, per os, model of experiment a) | | | | |
| 52 ± 3 | 45 ± 5 | 40 ± 3 | 40 ± 2 | 33 ± 4 |
| Composition 6, per os, model of experiment a) | | | | |
| 52 ± 3 | 46 ± 5 | 41 ± 3 | 40 ± 2 | 32 ± 4 |
| Composition 7, per os, model of experiment a) | | | | |
| 52 ± 3 | 55 ± 5 | 53 ± 3 | 53 ± 2 | 50 ± 5 |
| Focal ischemia without therapy | | | | |
| 52 ± 4 | 54 ± 5 | 53 ± 5 | 53 ± 3 | 52 ± 4 |
| False surgery operated animals | | | | |
| 32 ± 12 | 29 ± 15 | 27 ± 12 | 18 ± 7 | 12 ± 5 |
| Focal ischemia + hypothermia | | | | |
| 62 ± 4 | 57 ± 5 | 55 ± 7 | 45 ± 5 | 35 ± 4 |

The administration of compositions containing Creatine amides substantially reduced latency of movement initiation at the early period after the induction of FCI, i.e. after 1 and 3 days. Concerning this effect, the group with administration of the examined sample composition, insubstantially differs from the positive control group (hypothermia) and the group of FO animals.

In the process of analysis of animals behavior in an 'open field' installation, an expressed influence of the intra-peritoneal injection of Creatine amides at one of the physiological condition parameters of animals, having chronic FCI, was noticed, which parameter was latency of movement initiation that reflects a level of disorder of the neurons structure and inter-neuronal bonds.

The data concerning latency of movement initiation in the following groups of rats; a group with intra-peritoneal injections of the composition (n=7), a group with negative (n=13) control, a group with positive (n=5) control, and a group with false surgery operated animals (n=5) were compared one day before and 1, 3, and 7 days after FCI.

The movement initiation (also known as 'warm-up') is a complex multi-stage motor reaction of an organism to the internal and/or external stimulus).

In accordance with the procedure proposed by Golani et al (Golani I, Wolgin D L, Teitelbaum, P., 1979) for evaluation of the warm-up time, which was necessary for animal to leave beyond a squared area of 20×20 cm, located in a center of the 'open field' installation (1×1×0.5 m) was measured. The obtained results are presented in the Table 5.

TABLE 5

The data of animals behavioral testing in 'open field' (composition 2, experiment a)

| Impact | Latency of warm-up, s | | | |
|---|---|---|---|---|
| | 1 day before ischemia | 1 day after ischemia | 3 days after ischemia | 7 days after ischemia |
| FCI | 9 ± 2 | 49 ± 4 | 46 ± 4 | 16 ± 3 |
| FCI + composition 2 | 9 ± 2 | 25 ± 6 | 30 ± 8 | 10 ± 2 |
| FCI + hypothermia | 8 ± 2 | 10 ± 8 | 5 ± 2 | 2 ± 2 |

Administration of Creatine amides leads to a significant reduction of the brain damage area initiated by experimental ischemia (Table 6).

TABLE 6

The parameters of brain damage initiated by the experimental ischemia/post-ischemia reprefusion in rats associated with the amides of Creatine administration

| Sample, quantity of animals (n) | Ratio of a damage area to an area of the total coronal section of the brain (%) |
|---|---|
| Control, saline, i.e.v. injection, model of experiment (c), (n = 6) | 17.0 ± 1.8 |
| Composition 8, i.e.v. injection model of experiment (c), (n = 5) | 10.3 ± 1.0 |
| Composition 9, i.e.v. injection, model of experiment (c), (n = 5) | 11.9 ± 2.0 |
| Composition 10 i.e.v. injection, model of experiment (c), (n = 6) | 8.4 ± 0.7 |

The above-presented data indicate substance compositions, containing Creatine amides, are capable of producing a neuro-protective effect in the conditions of ischemia of the brain tissue. The compositions based on Creatine amides positively affect the rehabilitation of cognitive functions after experimental stroke and latency of the 'warm-up', characterizing a general condition of the energy tissue metabolism of the brain tissue in animals, the functional condition of the neurons and the associative areas of the cerebral cortex.

The invention claimed is:

1. Amides of Creatine having a general formula: $NH\!\!=\!\!C(NH_2)\text{-}N(CH_3)\text{-}CH_2\text{-}CO\!-\!NH\!-\!R^*X$, wherein R is amino acid residue of aliphatic L-amino acid, or aromatic amino L-acid or heteroaromatic L-amino acid or derivatives of aliphatic L-amino acid, or aromatic L-amino acid or heteroaromatic L-amino acid representing at least one of the following: salts of amino acid, amino acid esters, amino acid amides, or amino acid peptides; and X is low-molecular-weight organic or mineral acid or water.

2. A method for preparation of said amides of Creatine according to claim 1, said method comprising: interaction of amides of sarcosine and amino acids or their derivatives with guanidinylating agents in an organic solvents at a temperature not exceeding 50° C.

3. A compound possessing neuroprotective activity, said compound consisting of: amides of Creatine having a general formula: $NH\!\!=\!\!C(NH_2)\!-\!N(CH_3)\!-\!CH_2\!-\!CO\!-\!NH\!-\!R^*X$; wherein R is amino acid residue of aliphatic L-amino acid, or aromatic amino L-acid or heteroaromatic L-amino acid, or derivatives of aliphatic L-amino acid, or aromatic L-amino acid, or heteroaromatic L-amino acid representing at least one of the following: salts of amino acid, amino acid esters, amino acid amides, or amino acid peptides; and X is low-molecular-weight organic or mineral acid or water as a remedy possessing a neuroprotective activity.

* * * * *

UNITED STATES PATENT AND TRADEMARK OFFICE
CERTIFICATE OF CORRECTION

PATENT NO. : 8,350,077 B2  
APPLICATION NO. : 12/734183  
DATED : January 8, 2013  
INVENTOR(S) : Burov et al.

Page 1 of 1

It is certified that error appears in the above-identified patent and that said Letters Patent is hereby corrected as shown below:

The title page, item (75) should be corrected as follows:

Inventors: Burov; Sergej Vladimirovich (Saint-Petersburg, RU),
"Khromova; Natalia Vasilyevna (Saint-Petersburg, RU), Khromova; Anna Alexandrovna
(Saint-Petersburg, RU), Khromov; Petr Alekseevich (Saint-Petersburg, RU)"
-- Khromov; Aleksey Nikolayevich (Saint-Petersburg, RU) --

Signed and Sealed this
Twenty-fifth Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 8,350,077 B2
APPLICATION NO. : 12/734183
DATED : January 8, 2013
INVENTOR(S) : Sergej Vladimirovich Burov et al.

It is certified that error appears in the above-identified patent and that said Letters Patent is hereby corrected as shown below:

TITLE PAGE:

Item [75],

"Inventors: Burov; Sergej Vladimirovich (Saint-Petersburg, RU),
"Khromova; Natalia Vasilyevna (Saint-Petersburg, RU), Khromova; Anna Alexandrovna (Saint-Petersburg, RU), Khromov; Petr Alekseevich (Saint-Petersburg, RU)"
-- Khromov; Aleksey Nikolayevich (Saint-Petersburg, RU) --"

(as corrected to read in the Certificate of Correction issued August 25, 2015) is deleted and patent is returned to its original state with the Inventors name in patent to read -- Sergej Vladimirovich Burov, Saint-Petersburg (RU); Natalia Vasilyevna Khromova, Saint-Petersburg (RU); Anna Alexandrovna Khromova, Saint-Petersburg (RU); Petr Alekseevich Khromov, Saint-Petersburg (RU) --

Signed and Sealed this
Twenty-second Day of December, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,350,077 B2 | Page 1 of 1 |
| APPLICATION NO. | : 12/734183 | |
| DATED | : January 8, 2013 | |
| INVENTOR(S) | : Burov et al. | |

It is certified that error appears in the above-identified patent and that said Letters Patent is hereby corrected as shown below:

This certificate supersedes the Certificate of Correction issued December 22, 2015. The certificate is vacated since the inventor to be added was properly entered on OATH in the appropriate section for deceased inventors. The inventor, Khromov, Aleksey Nikolayevich, should have been included on the front page of patent. The Certificate of Correction dated December 22, 2015, was published in error and should not have been issued for this patent. The inventors set forth in printed patent are:

-- "Inventors: Burov; Sergej Vladimirovich (Saint-Petersburg, RU),
 "Khromova; Natalia Vasilyevna (Saint-Petersburg, RU), Khromova; Anna Alexandrovna
 (Saint-Petersburg, RU), Khromov; Petr Alekseevich (Saint-Petersburg, RU)"
 -- Khromov; Aleksey Nikolayevich (Saint-Petersburg, RU) --" --.

Signed and Sealed this
Twenty-third Day of February, 2016

Michelle K. Lee
*Director of the United States Patent and Trademark Office*